United States Patent [19]

Drake

[11] 4,259,262
[45] Mar. 31, 1981

[54] CATALYTIC HYDROGENATION OF UNSATURATED DINITRILES

[75] Inventor: Charles A. Drake, Bartlesville, Okla.

[73] Assignee: Phillips Petroleum Company, Bartlesville, Okla.

[21] Appl. No.: 69,200

[22] Filed: Aug. 23, 1979

[51] Int. Cl.³ .............................................. C07C 85/12
[52] U.S. Cl. .................................... 564/491; 252/447; 252/459; 252/466 PT; 564/511
[58] Field of Search ....................... 260/583 P, 583 K; 252/447, 459, 466 PT

[56] References Cited

U.S. PATENT DOCUMENTS

| | | | |
|---|---|---|---|
| 2,532,312 | 12/1950 | Romilly | 260/465.8 |
| 3,048,635 | 8/1962 | Indest et al. | 260/583 P |
| 3,189,643 | 6/1965 | Elam et al. | 260/468 |
| 3,350,439 | 10/1967 | Feldman et al. | 260/465.5 |
| 3,372,195 | 3/1968 | Little | 260/570.7 |
| 3,696,153 | 10/1972 | Kershaw et al. | 260/583 K |
| 3,896,174 | 7/1975 | Drake | 260/583 P |
| 3,987,099 | 10/1976 | Hockele et al. | 260/584 R |
| 4,025,561 | 5/1977 | Suggitt et al. | 260/583 K |
| 4,053,515 | 10/1977 | Drake | 260/583 P |

Primary Examiner—John Doll

[57] ABSTRACT

The catalytic hydrogenation of an unsaturated dinitrile reactant of the formula

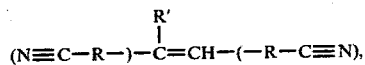

wherein each R is an alkylene or an alkylidene radical, and each R' is an alkyl radical, is carried out in the presence of ammonia, hydrogen, a suitable diluent and a catalyst selected from elemental ruthenium, a ruthenium compound which is reducible by hydrogen to elemental ruthenium and mixtures thereof on a granular catalyst support.

12 Claims, No Drawings

CATALYTIC HYDROGENATION OF UNSATURATED DINITRILES

This invention relates to a catalyst and to a process for the preparation of saturated aliphatic diamines by the catalytic hydrogenation of unsaturated aliphatic dinitriles.

U.S. Pat. No. 3,896,174 discloses that a catalyst selected from the group consisting of elemental ruthenium, ruthenium compounds which are reducible by hydrogen to elemental ruthenium, and mixtures thereof (referring to hereinafter as the "ruthenium catalyst") can be utilized in the hydrogenation of unsaturated aliphatic dinitriles having the formula:

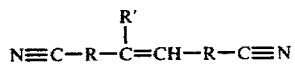

where each R is an alkylene or an alkylidene radical and each R' is an alkyl radical, while such disclosure is a valuable contribution to the art, an improvement in the catalyst life of the ruthenium catalyst disclosed in the patent is desirable to allow the hydrogenation process to be carried out at lower temperatures thus resulting in improved catalyst life. It is thus an object of this invention to increase the activity of a ruthenium catalyst and also to provide an improved process for the catalytic hydrogenation of unsaturated aliphatic dinitriles.

In accordance with the present invention, a granular support is utilized to support the ruthenium catalyst. The ruthenium catalyst can be added to the solid granular support by any of the methods well known in the art. Once the catalyst has been prepared, the unsaturated aliphatic dinitriles are hydrogenated in the presence of the catalyst to produce saturated aliphatic diamines.

The use of the granular support for the ruthenium catalyst provides an increase in the activity of the ruthenium catalyst. The increase in catalyst activity provides the potential of the use of milder hydrogenation conditions with resulting longer catalyst life and lower operating cost.

Other objects and advantages of the present invention will be apparent from the detailed description of the invention and the appended claims.

The branched-chain unsaturated aliphatic dinitriles which are considered to be advantageously and efficiently hydrogenated in accordance with the process of this invention are the unsaturated dinitriles of the general formula:

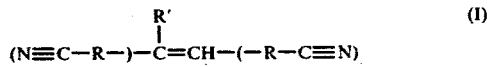

wherein each R is independently selected from the group consisting of an alkylene radical and an alkylidene radical, and R' is an alkyl radical. Each R will generally have from 1 to 15 carbon atoms, preferably from 1 to 6, and more preferably from 1 to 3 carbon atoms. R' will generally have from 1 to 15 carbon atoms, preferably from 1 to 6 carbon atoms, and more preferably from 1 to 3 carbon atoms. In general, the unsaturated dinitrile reactant of formula (I) will contain from 7 to 30 carbon atoms, preferably from 8 to 16 carbon atoms, and more preferably from 9 12 carbon atoms. Representative of unsaturated reactant species of formula (I) include such compounds as 4-methyl-3-hexenedinitrile, 4-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 1,2-dimethyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, and mixtures of any two or more thereof.

If desired, other unsaturated dinitrile reactants can be present and effectively hydrogenated during the hydrogenation of the unsaturated dinitriles of formula (I). Thus, in addition to the unsaturated dinitrile reactants of formula (I), the dinitrile feedstock can contain one or more unsaturated dinitrile reactants of the formula:

wherein each R" is independently selected from the group consisting of an alkylene radical and an alkylidene radical. In general, each R" will have from 1 to 15 carbon atoms, preferably from 1 to 7 carbon atoms, and more preferably from 1 to 4 carbon atoms. The dinitriles of formula (II) will generally contain from 6 to 30 carbon atoms, preferably from 8 to 16 carbon atoms, and more preferably from 9 to 12 carbon atoms. Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methyleneneonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylene-dodecanedinitrile, 2,4,8,10-tetrapropyl-6-methylenedodecanedinitrile, 2,2,6-dimethyl-14-methyleneheptacosanedinitrile, and mixtures of any two or more thereof.

Unsaturated dinitriles having a structure other than that of formulas (I) and (II) can be present during the hydrogenation reaction, if desired. Similarly, other compounds which may be found in the feed source of the dinitriles of formulas (I) and (II) can be present so long as such additional compounds do not significantly adversely affect the hydrogenation of the dinitriles of formulas (I) and (II). Where other dinitriles are present in the feedstock, the dinitriles of formula (I) will generally constitute at least 0.1 weight percent of the total dinitriles. The significant advantages of the invention increase with increasing concentrations of the dinitriles of formula (I) in the feedstock. Thus, the process of the invention is even more advantageous for concentrations of the dinitriles of formula (I) in the feedstock of at least 5 weight percent. The invention is considered to be particularly desirable for dinitrile feedstocks having a concentration of the dinitriles of formula (I) of at least 10 weight percent.

A presently preferred branched-chain unsaturated aliphatic dinitrile feedstock for employment in the practice of this invention is the dinitrile reaction product mixture obtained by the reaction of isobutylene and acrylonitrile. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonane-dinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type of formula (II). The weight ratio of the dinitriles of formula (I) to the dinitriles of formula (II) in this mixture is generally in the range of about 10:1 to about 1:10.

In the practice of this invention, the catalytic hydrogenation of the unsaturated dinitrile reactant of formula (I) results primarily in the formation of saturated diamine reaction products having the formula:

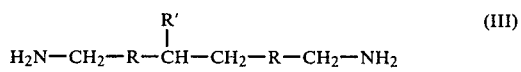

wherein R and R' are as defined hereinbefore. The catalytic hydrogenation of an unsaturated dinitrile reactant of formula (II) results primarily in the formation of saturated diamine reaction products having the formula:

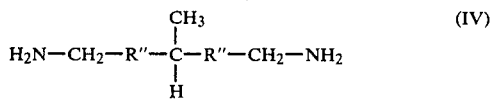

wherein R" is as defined hereinbefore.

The hydrogenation catalysts which are utilized in the present invention are those based on ruthenium. For example, the catalysts can be finely divided elemental urthenium, compounds of ruthenium which are reducible by hydrogen, at the hydrogenation conditions employed, to finely divided elemental ruthenium, and mixtures thereof. Suitable hydrogen reducible compounds include for example the oxides, halides, nitrates, oxalates, acetates, carbamates, propionates, tartrates, hydroxides, and the like, and mixtures of any two or more thereof. Specific examples include ruthenium oxide, ruthenium chloride, ruthenium nitrate, ruthenium acetate, ruthenium carbonate, ruthenium hydroxide and mixtures of any two or more thereof.

In the practice of this invention, the elemental ruthenium, reducible compound of ruthenium, or mixtures thereof are supported on a granular catalyst support. For the purpose of this invention, granular is defined as a material having approximately equal dimensions of length, width and height, but having an irregular shape. The surface of the granules when viewed with a magnification of about 7× to 10× is seen to be covered by tiny, irregular projections to form a heterogeneous surface. The size of the granular support is generally in the range of from about 0.5 inch (1.27 cm.) diameter to about 30 mesh (U.S. Standard Sieve Series, ASTM Specification E-11-61) with the limit on the finer size being determined by excessive pressure drop in the hydrogenation column and the limit on the coarser size being determined by excessive channeling of the feed between granules. The preferred size range for the granular support is in the range from about 4 to about 20 mesh. Specific supports (all in the granular shape) include, for example, carbon, kieselguhr, silica, alumina, silica-alumina, calcium carbonate, barium carbonate, asbestos, pumice, clays, and the like, and mixtures thereof. The presently preferred support is granular alumina.

The granular supports can be prepared by any suitable means, generally by crushing of larger bodies of the support material. For example, naturally occurring clays can be crushed and screened to the desired size. Synthetic support materials such as precipitated alumina can be compacted to relatively large pellets, extrudates, etc., then crushed to size to obtain the granular support.

The ruthenium catalyst can be added to the catalyst support by any of the methods well known in the art. For example, the supported catalysts can be prepared by dry mixing the components or by impregnating the granular support with a solution or dispersion of ruthenium in elemental form or in the form of reducible compounds thereof. The supported catalyst can be pretreated with hydrogen to reduce the compounds, or such reduction can be achieved in the hydrogenation reactor. The elemental ruthenium content of the supported catalyst will generally be in the range of about 0.01 to about 10 weight percent based on the weight of the granular support. For most efficient use of the catalyst metal the upper range is preferably limited to about 5 weight percent. To insure that sufficient catalyst metal is present the lower range is preferably limited to about 0.05 weight percent.

Specific examples of suitable supported ruthenium catalysts include 0.5 weight percent ruthenium on granular alumina, 0.2 weight percent ruthenium on granular silica, 0.5 weight percent ruthenium on granular carbon, and 1 weight percent ruthenium on granular alumina.

Any catalytic hydrogenation temperature can be employed which provides the desired degree of catalytic efficiency in the hydrogenation of the branched-chain saturated aliphatic dinitrile containing feedstock. The hydrogenation temperatures will generally be within the range of about 30° to about 250° C. The effective catalytic hydrogenation temperatures are preferably within the range of about 100° to about 250° C. and more preferably are within the range of about 100° to about 180° C.

The catalytic hydrogenation of branched-chain unsaturated aliphatic dinitriles can be carried out at any hydrogen pressure wherein both the olefinic unsaturation and the nitrile groups are reduced in the presence of ammonia, hydrogen and a suitable diluent. Generally, suitable hydrogen pressures are within the range of from about 100 to 5000 psig, but lower or even higher hydrogen pressures can be employed. Preferably, due to economic considerations, hydrogen pressures within the range of about 500 to about 3000 psig are employed. Higher hydrogen pressures may be desirable at lower reaction temperatures in order to achieve complete reduction within a reasonable reaction time.

The catalytic hydrogenation of unsaturated dinitriles in accordance with the process of this invention can be carried out as a continuous process at any suitable liquid hourly space velocity (LHSV). However, the liquid hourly space velocity rates will generally be within the range of about 0.01 to about 20, more preferably from about 0.1 to about 10, volumes of unsaturated dinitrile reactant plus diluent and ammonia per volume of catalyst (including the volume of catalyst support).

Any suitable diluent may be utilized in the hydrogenation process. The diluent is preferably selected from the class consisting of aliphatic teritary alcohols containing from 4 to 12 carbon atoms per molecule, unsubstituted acyclic and unsubstituted cyclic ethers having from 4 to 12 carbon atoms per molecule, and saturated hydrocarbons having 4 to 12 carbon atoms per molecule, and mixtures of any two or more thereof. The term "unsubstituted" signifies that there are no substituents other than hydrocarbyl radicals. It is preferred that the diluent be an aliphatic teritary alcohol or saturated hydrocarbon. Examples of alcohol diluents include 2-methyl-2-propanol, 2-methyl-2-butanol, 3-ethyl-3-hexanol, 2,4-dimethyl-2-pentanol, 2,3-dimethyl-3-pentanol, 3-ethyl-3-pentanol, 3,7-dimethyl-3-octanol, and the like and mixtures of any two or more thereof. The foregoing examples of saturated aliphatic alcohols are unsubstituted tertiary alkanols having at least 4 carbon atoms per molecule. Examples of alkanes and cycloalkanes include butane, pentane, hexane, decane, dodecane, cyclobutane, cyclopentane, cyclohexane, cyclodecane, cyclododecane, 2-methylbutane, methylcyclopentane, 2,2,4-trimethylpentane, and mixtures thereof. Examples of ethers include 1,3-dioxane, 1,4-dioxane, tetrahydrofuran, 4,4-dimethyl-1,3-dioxane, and mixtures of any two or more thereof. To facilitate handling of the reaction mixtures, the weight ratio of unsaturated dinitrile reactants to diluent charged to the reaction zone is generally within the weight ratio range of about 0.001:100 to about 35:100, and is preferably in the range of about 0.1:100 to about 25:100.

Ammonia is employed in the process of this invention as a means of suppressing undesirable side reactions such as the formation of secondary and tertiary amines. Any amount of ammonia can be employed which is effective in deterring or reducing undesirable side reactions. In general, the mol ratio of ammonia to cyano group (there being two cyano groups in each unsaturated dinitrile) will be in the range of about 1:1 to about 25:1, and preferably will be in the range of about 3:1 to about 20:1.

Recovery of the desired end product, the branched-chain saturated aliphatic diamines, as well as any resulting reaction byproducts, any unconsumed reactants, ammonia, hydrogen, and/or diluents can be carried out by any conventional separation means. In general, at the conclusion of the catalytic hydrogenation process, the reaction effluent is cooled and depressurized with the recovery, if desired, to any ammonia or diluent which is vented from the reaction effluent during the depressurization operation. The ammonia or diluent can be returned or recycled to the hydrogenation zone if desired.

The following examples are presented in further illustration of the invention.

The hydrogenation substrate which was utilized in Example I and Example II was an unsaturated dinitrile mixture obtained by the reaction of isobutylene and acrylonitrile. This unsaturated dinitrile mixture comprised approximately 52 weight percent 5-methylenenonanedinitrile, aproximately 35 weight percent 5-methyl-4-nonenedinitrile, approximately 12 weight percent of the combination of 2,4-dimethyl-4-octenedinitrile, 2-methyl-4-methyleneoctanedinitrile, and 2,4-dimethyl-3-octenedinitrile, and approximately 1 weight percent of the combination of 2,6-dimethyl-4-methyleneheptanedinitrile and 2,4,6-trimethyl-3-heptenedinitrile. For convenience, the above mixtures will be referred to as diadduct.

All of the runs described in Example I and Example II were carried out in a 0.5" (12.7 mm) diameter ×20" (508 mm) length continuous reactor fitted with a steam heating system and temperature recorder.

EXAMPLE I

Three runs were carried out in which diadduct was hydrogenated over supported ruthenium catalysts containing 0.5 weight percent Ru based on the support weight. The catalyst in each run was prepared by impregnating the support with ruthenium chloride from a methanol solution, drying, and reducing in the presence of hydrogen at 400° C. for three hours. In each run, the continuous reactor was charged with 20 g (about 20 ml) of the supported catalyst, flushed with nitrogen, and flushed with hydrogen at a rate of 1 liter per minute at 140°. A mixture containing diadduct, 2-methyl-2-propanol, and ammonia in a weight ratio of 1/8/1 was fed to the reactor at a LHSV of about 6. Reactor conditions during the hydrogenation were 140° C., 1500 psig (10.3 MPa) pressure, and 1 liter per minute hydrogen flow. Samples were collected from the reactor effluent after 4 hours of run time and after 19 hours of run time and each sample was analyzed by gas-liquid chromatography after removal of the diluent and ammonia.

The catalyst support in run 1 was a commercial ⅛" alumina tablet. The catalyst support in run 2 was a commercial 1/16" alumina extrudate. Run 3 utilized a granular alumina support prepared by grinding ⅛" alumina tablets in a grinding mill and sieving the product to a 8 to 14 mesh range. The results of the hydrogenation runs are presented in Table I.

TABLE I

| Run No. | Alumina Support | Support Surface Area, $M^2/g^{(a)}$ | Saturated Diamines, Weight $\%^{(b)}$ 4 hrs. | 19 hrs. |
|---|---|---|---|---|
| 1 | ⅛"Tablets | 233 | 25 | 12 |
| 2 | 1/16"Extrudate | 232 | 62 | 32 |
| 3 | 8-14 Mesh Granules | 210 | 76 | 48 |

$^{(a)}$Determined by nitrogen adsorption. $^{(b)}$Weight percent saturated diamines present in the reaction product at the indicated time during the run with the percent being based on the product weight after removal of the diluent and ammonia.

The results of the runs in Table I show that although all three supports have similar surface areas as determined by the nitrogen adsorption method, the ruthenium catalyst on a granular alumina support resulted in a significantly higher yield of the desired saturated diamine product than ruthenium on either tablets or extrudate.

EXAMPLE II

Two runs were carried out in which diadduct was hydrogenated over supported ruthenium catalysts containing 0.5 weight percent Ru based on the support weight. The catalyst in each run was prepared by impregnating the support with ruthenium chloride from a methanol solution, drying, and reducing at 300° C. for 3 hours. The support in run 4 was a commercial 1/16" alumina extrudate and the support in run 5 was a commercial 8 to 14 mesh granular alumina. In each run, the continuous reactor was charged with 15 g. (about 15 ml) of the supported catalyst, flushed with nitrogen, flushed with hydrogen at a rate of 1 liter per minute at 150° C. A mixture containing diadduct, 2-methyl-2-propanol, cyclohexane, and ammonia in a weight ratio of 1/4.8/3.2/1 was fed to the reactor at a LHSV of about 4. Reactor conditions during the hydrogenation were 150° C., 1500 psig (10.3 MPa) pressure, and 1 liter per minute hydrogen flow. Samples were collected from the reactor effluent after 3 or 4 hours and after 19 or 20 hours of run time and each sample was analyzed by glc after removal of the diluents and ammonia. The results of these runs are presented in Table II.

TABLE II

| Run No. | Alumina Support | Saturated Diamine, Weight %[a] | |
|---|---|---|---|
| | | 3 or 4 hrs. | 19 or 20 hrs. |
| 4 | 1/16" Extrudate | 82 | 65 |
| 5 | 8-14 Mesh Granules | 99 | 95 |

[a]Weight percent saturated diamines present in the reaction product at the indicated time during the run with the percent based on the product after removal of the diluents and ammonia.

The results presented in Table II show that the use of a granular alumina support for the ruthenium hydrogenation catalyst results in a significantly higher yield of the desired saturated diamine product than an alumina extrudate support.

The foregoing examples illustrate that a ruthenium catalyst on granular support is a more active catalytic agent for the hydrogenation of unsaturated aliphatic dinitriles than a ruthenium catalyst on another type of support.

Reasonable variations and modifications are possible within the scope of the disclosure and the appended claims to the invention.

What is claimed is:

1. A process for the catalytic hydrogenation of an unsaturated dinitrile feedstock comprising at least one unsaturated dinitrile compound of the formula

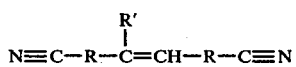

wherein each R is independently selected from the group consisting of an alkylene radical and an alkylidene radical, R' is an alkyl radical, and the number of carbon atoms in said compound is in the range of 7 to 30; which comprises contacting said feedstock under suitable hydrogenation conditions in a reaction zone with ammonia; hydrogen; and a catalyst composition consisting essentially of a catalytic component selected from elemental ruthenium, ruthenium compounds which are reducible by hydrogen to elemental ruthenium at said suitable hydrogenation conditions, and mixtures thereof supported by a granular catalyst support; in a suitable diluent to thereby effect the hydrogenation of said at least one unsaturated dinitrile compound to the corresponding branched-chain saturated aliphatic diamine, wherein said granular catalyst support has a diameter in the range of from about 0.5 inch (1.27 cm) diameter to about 30 mesh.

2. A process in accordance with claim 1 wherein said granular catalyst support is selected from the group consisting of carbon, kieselguhr, silica, alumina, silica-alumina, calcium carbonate, barium carbonate, asbestos, pumice, clays, and mixtures of any two or more thereof.

3. A process in accordance with claim 2 wherein said granular catalyst support is granular alumina.

4. A process in accordance with claim 1 wherein said granular catalyst support has a diameter in the range of from about 4 mesh to about 20 mesh.

5. A process in accordance with claim 1 wherein the granules which make up said granular catalyst support have approximately equal dimensions of length, width and height.

6. A process in accordance with claim 1 wherein the content of the elemental ruthenium in said catalyst composition is in the range of about 0.01 to about 10 weight percent based on the weight of said granular catalyst support.

7. A process in accordance with claim 1 wherein the content of the elemental ruthenium in said catalyst composition is in the range of about 0.05 to about 5 weight percent based on the weight of said granular catalyst support.

8. A process in accordance with claim 1 wherein said feedstock further comprises at least one unsaturated dinitrile reactant of the formula:

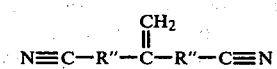

wherein each R" is independently selected from the group consisting of an alkylene radical and an alkylidene radical, and the number of carbon atoms in said reactant is in the range of 7 to 30.

9. A process in accordance with claim 1 wherein each of said alkylene radical, said alkylidene radical and said alkyl radical has from 1 to 15 carbon atoms.

10. A process in accordance with claim 1 wherein said at least one unsaturated dinitrile compound comprises a mixture of 5-methyl-4-nonenedinitrile, 2,4-dimethyl-4-octenedinitrile, 2,4-dimethyl-3-octenedinitrile, and 2,4,6-trimethyl-3-heptenedinitrile.

11. A process in accordance with claim 1 wherein said suitable diluent consist essentially of at least one component selected from the group consisting of unsubstituted tertiary alkanols having from 4 to 12 carbon atoms per molecule, unsubstituted acyclic and unsubstituted cyclic and unsubstituted cyclic ethers having from 4 to 12 carbon atoms per molecule, and saturated hydrocarbons having from 4 to 12 carbon atoms per molecule.

12. A process in accordance with claim 1 wherein said hydrogenation conditions comprise a mol ratio of ammonia to cyano groups in the range of about 1:1 to about 25:1, a hydrogen pressure in the range of about 100 to about 5000 psig, a weight ratio of the unsaturated dinitriles to the diluent in the range of about 0.001:100 to about 35:100, a temperature in the range of about 30° to about 250° C., and a liquid hourly space velocity rate in the range of about 0.01 to about 20 volumes of unsaturated dinitrile plus diluent and ammonia per volume of catalyst.

* * * * *